US00PP11634P

United States Patent [19]

Zary

[11] Patent Number: Plant 11,634

[45] Date of Patent: Nov. 14, 2000

[54] HYBRID TEA ROSE PLANT NAMED 'JACUNU'

[75] Inventor: Keith W. Zary, Thousand Oaks, Calif.

[73] Assignee: Bear Creek Gardens, Inc., Medford, Oreg.

[21] Appl. No.: 09/234,789

[22] Filed: Jan. 20, 1999

[51] Int. Cl.[7] ..... A01H 5/00

[52] U.S. Cl. ..... Plt./134

[58] Field of Search ..... Plt./130, 133, 134

*Primary Examiner*—Howard J. Locker

*Attorney, Agent, or Firm*—Klarquist Sparkman Campbell Leigh & Whinston, LLP

[57] ABSTRACT

Hybrid tea rose plant having strong, vigorous, upright growth, very good cut flower production of flowers of heavy petal substance on long, strong stems having long vase life.

1 Drawing Sheet

The present invention relates to a new and distinct variety of rose plant of the hybrid tea rose class which was originated by me by crossing the variety 'KORenlo', U.S. Plant Pat. No. 5,679, with the variety 'JACkar', unpatented, ('JAClopi', U.S. Plant Pat. No. 5,859×'KORlingo', U.S. Plant Pat. No. 5,846).

The primary objective of this breeding was to produce a new rose variety having the high cut flower production and vigorous growth of the female parent combined with the heavy petal substance, good vase life, and strong steams of the male parent. The objective was substantially achieved, along with other desirable improvements, as evidenced by the following unique combination of characteristics that are outstanding in the new variety and that distinguish it from its parents, as well as from all other varieties of which I am aware:

1. Stong, vigorous, upright growth;
2. Heavy petal substance;
3. Very good cut flower production;
4. Long vase life, and;
5. Long, strong stems.

'JACunu' is a greenhouse cut flower rose. Production is 180–200 stems/m$^2$ of greenhouse with stems between 22–26" long. Vase life is about twelve days.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'KORenlo' (U.S. Plant Pat. No. 5,679).

*Pollen parent.*—'JACkar' (unpatented, ('JAClopi', U.S. Plant Pat. No. 5,859×'KORlingo', U.S. Plant Pat. No. 5,846)).

Classification:

*Botanical.*—*Rosa hybrida.*

*Commercial.*—Hybrid Tea.

FLOWER

Observations made from specimens grown in a greenhouse environment at Somis, Calif., Feburary 1997 to December 1998.

Blooming habit: Continuous.

Bud:

*Size.*—One and three-fourths inches long when the petals start to unfurl.

*Form.*—The bud form is long, pointed ovoid.

*Color.*—When sepals first divide, bud color is Yellow Group 10C. When half blown, the upper sides of the outer petals are White Group 155D on the outer two-thirds of a petal, the inner one-third being Yellow Group 10C. The inner petals are Yellow Group 10C on their upper sides. The lower sides of the petals are very similar to the upper sides.

*Sepals*—Color: Green Group 138B. Surface texture: Covered in fine hairs. There are three normally to heavily appendaged sepals. There are two unappendaged sepals with hairy edges.

*Receptacle.*—Color: Green Group 137D. Shape: Funnel. Size: Medium, about 7/16"×3/8". Surface: Smooth.

*Peduncle.*—Length: Long, averaging about 4½ inches. Surface: Prickly with several very small prickles. Color: Green Group 137C. Strength: Stiff, erect.

Bloom:

*Size.*—Large. Average open size is five inches.

*Borne.*—Singly.

*Stems.*—Strength Strong. Average length is about twenty-two to twenty-six inches.

*Form.*—When first open: High-centered. Permanence: Retains its forms to the end, outer petals curl back in quill fashion.

*Petalage.*—Number of petals under normal conditions: 30–35.

*Color.*—The upper sides of the petals are white Group 155D on the outer two-thirds of the outer petals. The inner one-third of the outer petals are Yellow Group 10C. The inner petals are Yellow Group 10C on their upper sides. The reverse sides of the petals are very similar to the upper sides. The base of each petal has on the upper side a small (1/8"×1/8"), Yellow Group 9B color spot at the point of attachment. The lower side has a smaller (1/6"×1/16") Yellow Group 9C color spot. The major color on the upper side is Yellow Group 10C.

*Variegations.*—None.

*Discoloration*.—The general tonality at the end of the first day: No change. At the end of the third day: Some fading on outer petals from Yellow Group 10C to White Group 155D. There is a gradual change from Yellow Group 10C to White Group 155D. By day eight on the plant, the entire petal is White Group 155D except for the color spot at the point of attachment.

*Fragrance*.—Slight.

Petals:

*Texture*.—Thick.

*Shape*.—Deltoid.

*Form*.—Tips slightly recurved, edges slightly quilled.

*Arrangement*.—Imbricated. Petaloids in the center: None.

*Persistence*.—Petals drop off cleanly before drying.

*Lastingness*.—On the plant: Long (about eight days). As a cut flower: Long (about twelve days).

Reproductive parts:

*Anthers*.—Size: Medium. Quantity: Many. Color: Yellow-Orange Group 22D. Arrangement: Regular around styles.

*Filaments*.—Color: Yellow Group 5C.

*Pollen*.—Present

*Styles*.—Color: Yellow-Green Group 149D.

*Stigmas*.—Color: Yellow Group 2C.

Plant:

*Form*.—Bush.

*Growth*.—Vigorous. Maturity plant height is about 5½ feet, width is about 3½ feet.

Foliage: Number of leaflets on normal mid-stem leaves: Five.

*Size*.—Large (6½" long×5¾" wide).

*Quantity*.—Abundant.

*Color*.—New foliage: Upper and lower surfaces: Greyed-Red Group 178A. Old foliage: Upper surface: Green Group 137A. Lower surface: Green Group 138B.

Leaflets:

*Shape*.—Broadly oval.

*Texture*.—Leathery.

*Edge*.—Serrated.

*Serration*.—Single, small.

*Petiole rachis*.—Color: Yellow-Green Group 147C with younger leaves having Greyed-Purple Group 187A on the upper surface of the petiole.

*Petiole underside*.—Smooth with a few prickles.

*Stipules*.—Medium (about 9/16"), serrated, bearded.

*Disease resistance*.—Resistant to rust but susceptible to mildew under normal growing conditions in a greenhouse. Not tested for blackspot.

Wood:

*New wood*.—Color: Yellow-Green Group 146C. Bark: Smooth.

*Old wood*.—Color: Green Group 137C. Bark: Smooth.

Prickles:

*Quantity*.—On main canes from base: Ordinary. On laterals from main canes: Ordinary.

*Form*.—Medium, hooked downward.

*Color when young*.—Greyed-Orange Group 166A.

*Color when Mature*.—Greyed-Orange Group 176C.

Small Prickles:

*Quantity*.—On main Stalks: None. On laterals: None.

I claim:

1. A new and distinct variety of rose plant of the hybrid tea class, substantially as herein shown and described, characterized particularly by its strong, vigorous, upright growth, very good cut flower production of flowers of heavy petal substance on long, strong stems having long vase life.

* * * * *

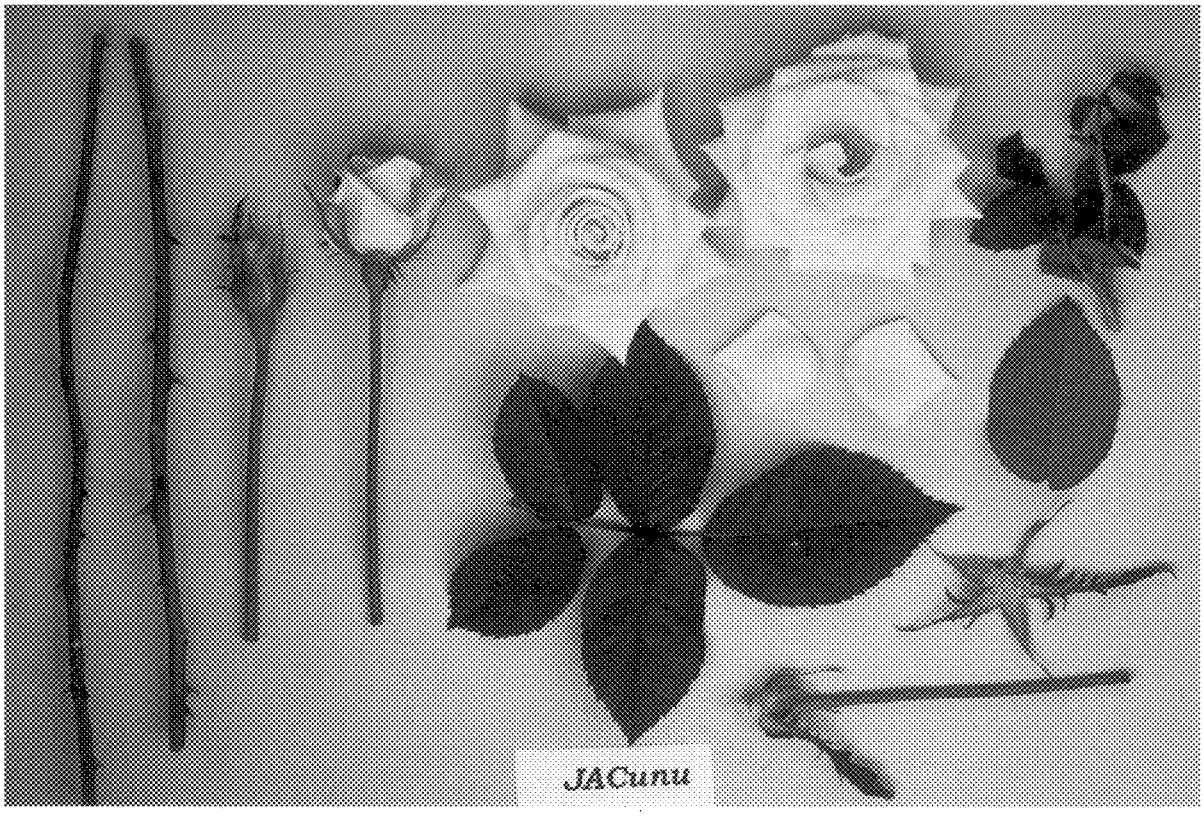
JACunu